United States Patent [19]

Messing et al.

[11] 4,071,409

[45] Jan. 31, 1978

[54] IMMOBILIZATION OF PROTEINS ON INORGANIC SUPPORT MATERIALS

[75] Inventors: Ralph A. Messing, Horseheads; Sidney Yaverbaum, Suffern, both of N.Y.

[73] Assignee: Corning Glass Works, Corning, N.Y.

[21] Appl. No.: 688,469

[22] Filed: May 20, 1976

[51] Int. Cl.[2] .............................................. C07G 7/02
[52] U.S. Cl. ...................................... 195/63; 195/68; 195/DIG. 11; 195/103.5 A; 260/112 R
[58] Field of Search .................... 195/63, 68, DIG. 4, 195/103.5 A; 260/112 R

[56] References Cited

U.S. PATENT DOCUMENTS

| 3,519,538 | 7/1970 | Messing et al. | 195/63 |
| 3,672,955 | 6/1972 | Stanley | 195/68 |
| 3,705,084 | 12/1972 | Reynolds | 195/63 |
| 3,796,634 | 3/1974 | Haynes et al. | 195/63 |

OTHER PUBLICATIONS

Hustad et al., Immobilization of Beta-Galactosidase on an Insoluble Carrier With a Polyisocyanate, I. Preparation and Properties, J. Da. Sci., vol. 56 1973 (pp. 1111-1117).

*Primary Examiner*—David M. Naff
*Attorney, Agent, or Firm*—James A. Giblin; Clinton S. Janes, Jr.; Clarence R. Patty, Jr.

[57] ABSTRACT

Biologically active proteins such as enzymes and antibodies can be chemically bonded to a variety of high surface area, inorganic supports by reacting the support surface with polymeric isocyanates and then reacting the coated surface with a dispersion of the proteins.

8 Claims, No Drawings

IMMOBILIZATION OF PROTEINS ON INORGANIC SUPPORT MATERIALS

BACKGROUND OF THE INVENTION

1. Field

The present invention is concerned generally with the immobilization of biologically active proteins and specifically with the chemical attachment of such proteins to high surface area inorganic supports.

2. Prior Art

A variety of techniques have been devised to immobilize various biologically active proteins such as enzymes and antibodies onto and within high surface area inorganic supports. See, for example, U.S. Pat. No. 3,556,945 (enzymes adsorbed to porous glass); U.S. Pat. No. 3,804,719 (enzymes crosslinked within the pores of porous glass); U.S. Pat. No. 3,519,538 (enzymes coupled via intermediate silanes to various inorganics); U.S. Pat. No. 3,652,761 (antibodies coupled via silanes to various inorganics); U.S. Pat. No. 3,850,751 (enzymes adsorbed within the pores of various ceramics); U.S. Pat. No. 3,839,175 (enzymes immobilized via electrodeposition on various porous ceramics); U.S. Pat. No. 3,930,951 (enzymes coupled via BMBD to inorganics); U.S. Pat. No. 3,912,593 ("chelation" of various biologically active materials to oxides of certain metals); U.S. Pat. No. 3,933,589 (enzymes coupled via a mixture of dialkylamines and alkane dihalides to inoganics); and U.S. Pat. No. 3,705,084, enzymes bonded to the surfaces of various macroporous reactors. Methods of covalently bonding proteins to various organic polymers using cyanates are disclosed in U.S. Pat. No. 3,788,948. Although the above list is not intended to be complete, it is clear that a wide variety of methods have been discovered for attaching biologically active proteins to inorganic materials. Most of the above discoveries are relatively recent, thus indicating the present need for exploring alternative methods for immobilizing proteins in an acceptably active state on the surfaces of inorganic supports. Although the presently known bonding techniques have various advantages and disadvantages relative to each other, and to similar techniques used with organic carriers, we have now found a novel method of bonding proteins to inorganic surfaces using a relatively inexpensive and simple class of polymers previously not used. Details of our immobilization method are described in detail herein.

SUMMARY OF THE INVENTION

Our method of bonding biologically active proteins to the surfaces of high surface area inorganic support materials comprises the steps of reacting an organic solution of polymerized isocyanate compounds having a molecular weight of at least about 250 with a high surface area inorganic material having surface hydroxyl or oxide groups to form a polymeric surface having reactive isocyanate groups, and then reacting the treated support with a dispersion of the proteins under conditions sufficient to assure bonding of the protein in a biologically active state to the surface of the support via the isocyanate groups. In preferred embodiments the inorganic support is titania, alumina, silica or porous glass, and the bonded proteins are enzymes or antibodies.

SPECIFIC EMBODIMENTS

The polymeric isocyanates useful for bonding the proteins may be represented as follows:

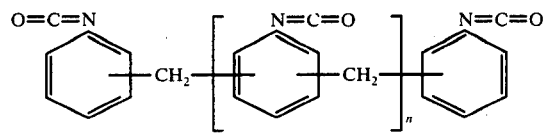

where $n$ is an interger having a value of at least 2. Such polymeric isocyanates are available commercially (e.g. sold under tradename PAPI, Polymer Chem. Div., Upjohn Company).

We have found that a very effective polymeric isocyanate for use with porous titania, silica, alumina is that sold under the tradename PAPI-901.

All of these polymeric isocyanates are insoluble in water and they must be applied from an organic solvent. We have found the most effective solvent is acetone. Toluene is also a good solvent for this purpose; however, since toluene is not readily soluble in water, and acetone is, we found that we can accomplish the attachment of the proteins much more rapidly when the solvent is acetone. Alcohols are not very useful as a solvent since they will react with the coupling agent to form urethanes. Solvents having either hydroxyl or amine groups should not be utilized for this coupling procedure since they react to form either urethanes or substituted ureas.

The reaction of the polymeric isocyanate coupling agent with the carrier (e.g. titania) results in the formation of a metal carbamate. This may be represented as follows:

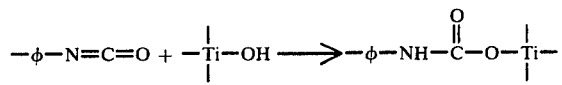

The isocyanate groups that have not reacted with the carrier remain available for coupling to the enzyme in the following manner: Reaction 1 (under alkaline conditions) — to yield substituted ureas.

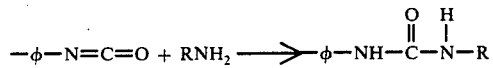

Reaction 2 (under mildly acid conditions) — to yield urethanes.

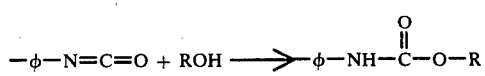

From the above, it can be seen that the polymeric isocyanates of this invention can be used under a variety of pH conditions, both alkaline and acidic.

For efficient and practical protein loading, the inorganic supports should have a high surface area (e.g. $>0.2$ m$^2$/g) and may be porous. A preferred average pore size range is about 100 to 2500A. Although any essentially water insoluble inorganic having surface hydroxyl or oxide groups capable of reacting with the polymer may be used, a very preferred support or carrier consists of porous titania particles, 30–80 mesh, having an average pore size in the range of about 320 to about 1500A.

Although $TiO_2$ is preferred as a support and was one of the carriers used in the illustrative examples below, inorganic supports consisting of silica, alumina, and porous glass were also used successfully to bond biologically active proteins via the polymeric isocyanate. Among the biologically active proteins successfully coupled to inorganic according to the methods disclosed herein were the enzymes papain, urease, glucoamylase, and lactase. A representative antibody (anti-digoxin) was also successfully coupled. The procedures used to couple the papain and anti-digoxin antibodies are described, for illustrative purposes, in the examples below.

EXAMPLES I AND II

Papain Coupled to Porous $TiO_2$ and $SiO_2$

In these examples, the polymeric isocyanate consisted of a 1% (v/v) solution of the PAPI 901 polymer. To prepare the solution, 0.25 ml of the PAPI-901 was diluted to 25 ml with acetone. The papain (0.2 Hoover Ball Milk Clot) was obtained from Nutritional Biochem. Co. The titania support consisted of porous $TiO_2$ particles (30/80 mesh) having an average pore diameter of about 420A and a surface area of 35 m$^2$/g. The porous silica particles (25/60 mesh) had an average pore diameter of 500A and a surface area of 50 m$^2$/g.

Preparation of Carrier Surfaces

Two 500 mg quantities of each titania and silica support (carrier) were placed in four 25 ml Erlenmeyer flasks. To each flask was added 1 ml of the coupling solution which was allowed to react with the carrier at room temperature for 5 minutes. The titania immediately reacted with the coupling agent to form an orange-coated porous body. The silica was somewhat slower to react but a yellow coating of coupling agent formed on the silica bodies. The color due to the coupling agent was completely removed from solution in the case of the titania porous bodies. The residual acetone solvent was decanted from the flask and the porous bodies were then ready for reaction with the enzyme.

The enzymes were then coupled to the treated carriers in two separate series (Series 1 under alkaline conditions and Series 2 under acidic conditions). The reactions were as follows:

Coupling of the Enzymes

Series 1 — immobilization from alkaline, pH 8.0, enzyme solution. One gram of the papain was diluted to 10 ml with 0.2 M $Na_2HPO_4$.

To one flask containing isocyanated titania and one flask containing isocyanated silica was added 10 ml of the above enzyme solution and the flasks were placed in a 23° C water bath with shaking for 7 hours. The flasks were then removed from the shaking water bath, the unreacted enzyme solution was decanted, and the immobilized enzymes were washed first with water, followed by 0.5 M sodium chloride and finally followed by water again.

Series 2 — immobilization from mildly acidic solutions, pH 5.2.

Enzyme solution — 1 gram of the papain was diluted to 10 ml with distilled water.

To each of the remaining 2 flasks, one containing the isocyanated titania and one containing the isocyanated silica, were added 10 ml of papain solution and the flasks were placed in a shaking water bath at 23° C. The flasks were shaken for 3 hours. The flasks were then removed from the bath and the unreacted enzyme solutions were decanted. The immobilized enzymes were first washed with water and then 0.5 M sodium chloride solution, followed by a final wash with water.

The series 1 and 2 immobilized enzymes were stored at room temperature in water between assays. The immobilized enzymes were assayed with 0.2% egg albumin solution in acetate buffer containing cysteine and EDTA at pH 5.0 at 37° C. The optical density of the trichloroacetic acid extract of the reacted substrate was determined at 280 nm and compared to a curve for the free enzyme to give the milligram of active papain per gram of carrier. These results are recorded below.

TABLE I

| | (mg active papain/g) | | | |
| | Series 1 | | Series 2 | |
| Days of Storage | $SiO_2$ | $TiO_2$ | $SiO_2$ | $TiO_2$ |
| --- | --- | --- | --- | --- |
| 1 | 73.4 | 58.6 | 115.7 | 63.8 |
| 4 | | 39.2 | 28.9 | 53.4 |
| 14 | 21.6 | 32.0 | 43.2 | 39.6 |
| 21 | 19.0 | 39.0 | 30.0 | 34.0 |

In previous immobilization studies that were performed with porous silica and porous glass, it was noted that most of the activity (99% or more) of papain was lost during the first 21 days of storage. In addition, on a per gram basis of carrier, the loadings were usually under 30 mg of papain. It is significant to note from the results above that there was little difference between the loading and stability on the titania of the alkaline and acid series. It would appear as though higher loadings were achieved under the acidic condition in the silica series.

COMPARISON WITH ADSORBED ENZYME

To have a basis for comparing the efficiency of the polymeric isocyanate as a coupling agent in a practical application (e.g. flow through column), the coupled enzyme composite was compared with an adsorbed enzyme system.

In preparing both the adsorbed (Column #1) and chemically coupled papain (Column #2) for comparison studies, the above described porous titania particles were used.

Column #1 — Adsorbed Immobilized Papain

Preparation of Enzyme for Immobilization 40 gms of the papain was dispersed to 400 ml with distilled water and transferred to dialysis tubing. The papain was dialyzed against 4 liters of distilled water at room temperature for 30 minutes. The dialysis water was then changed and dialysis was continued for 30 mins. Every half hour the dialysis water was changed and the dialysis was repeated. This was repeated for a total of 6 times. The final volume of the papain solution after dialysis was 485 ml.

Preparation of Carrier for Immobilization 400 ml of water was added to 20 gms of the porous titania particles in a flask. The flask was placed in a shaking water bath at room temperature for 1 hour and 20 mins. with shaking. The water was then decanted and 400 ml of 0.1 M $Na_2S_2O_3$ (pH 7.9) was added. The flask was shaken for 10 mins. at room temperature and the solution was then decanted. 400 ml of water was then added to the flask and shaking was repeated for 1 hour at room temperature. The water was decanted and the carrier was ready for immobilization.

Preparation of the Immobilized Enzyme

The 485 ml of dialyzed papain was added to the 20 gms of pretreated titania in a flask. The flask was immersed in a water bath at room temperature and allowed to shake overnight (approximately 17 hours). The enzyme solution was decanted and washed first with 500 ml of distilled water by shaking in a water bath for ½ hr. at room temperature and then with 500 ml of 0.5 M NaCl solution by shaking in a water bath for 1 hour at room temperature. After decantation of the sodium chloride solution, the immoblized (adsorbed) enzyme was finally washed with 3 washes of 500 ml of distilled water, each wash comprising 1 hour of shaking in the water bath at room temperature. The immobilized enzyme was then transferred to a water jacketed column which was controlled to 37° C. A 0.5% casein substrate containing cysteine and EDTA buffered to pH 6.1 with sodium acetate was pumped through the column at approximately 40 ml per hour.

Column #2 — Immobilized Papain by Chemically Coupling to Titania with Polymeric Isocyanate Preparation of Carrier for Coupling 40 ml of the PAPI-901 was added to 20 gms of the titania particles in a 500 ml Erlenmeyer flask. This was followed by the immediate addition of 500 ml of acetone. The sample was mixed and allowed to stand for 30 mins. at room temperature. The acetone containing the PAPI was decanted and the porous bodies were washed with 400 ml of distilled water. The water wash was immediately decanted and the carrier was utilized for coupling.

Immobilization of Papain by Chemically Coupling

A papain solution containing 40 gms of papain in 400 ml of water was immediately added to the polymeric isocyanate carrier and the flask with contents was placed in a water bath at room temperature with shaking for 3 hrs. The flask was then removed from the bath and allowed to stand at room temperature overnight (approximately 17 hours). The enzyme solution was decanted and samples were washed with distilled water several times. The immobilized enzyme was transferred to a water jacketed column at 37° C and the same substrate utilized for the adsorbed enzyme was pumped through the immobilized enzyme at 40 ml per hour.

Monitoring of Immobilized Enzyme Columns

Samples of the product collected from the columns were precipitated with trichloroacetic acid. The soluble extract was separated from the precipitate and analyzed at 280 nm. The % hydrolysis was obtained by comparing the optical density with that of a TCA extract of a 0.5% casein solution which had been completely hydrolyzed by papain with no subsequent reaction with papain. The % hydrolysis figure was then utilized for determining the grams of casein converted per hour. The results of these column studies are recorded in the following table.

TABLE II

| Days | (grams of casein converted per hour) | |
|---|---|---|
| | Column #1 | Column #2 |
| 3 | .155 | .120 |
| 4 | .135 | .120 |
| 5 | .165 | .150 |
| 6 | .135 | .120 |
| 7 | .155 | .130 |
| 10 | .120 | .120 |
| 11 | .115 | .115 |
| 12 | .105 | .120 |
| 13 | .095 | .100 |
| 14 | .095 | .105 |
| 17 | .080 | .090 |
| 18 | .080 | .095 |
| 19 | .070 | .090 |
| 20 | .050 | .090 |
| 21 | .060 | .075 |
| 24 | Column stopped, started without washing. | Column stopped, started without washing. |
| 25 | .095 | .085 |
| 26 | .075 | .080 |
| 27 | .075 | .065 |
| | | Washed IME |
| 32 | .050 | .120 |
| 33 | .050 | .120 |
| | Washed IME | |
| 34 | .105 | .115 |
| 35 | .115 | .105 |
| 38 | .080 | .105 |
| 39 | .075 | .105 |
| 40 | .075 | .105 |
| 41 | .075 | .105 |
| 42 | .065 | .095 |
| 45 | .060 | .120 |
| 46 | .050 | .115 |
| 47 | .055 | .120 |
| 48 | .055 | |
| 49 | .050 | |

These results were plotted and a linear regression was determined before the column was clogged up and then after the immobilized enzymes in each column were washed with water.

It is apparent from the results that the adsorbed enzyme exhibited an activity that was 22% greater than the coupled enzyme at the third day of operation. However, after 20 days of operation, the adsorbed enzyme exhibited an activity of 20–30% lower than that of the coupled enzyme. It is further apparent that after washing the coupled enzyme with water, this preparation was fully restored to its third day activity, while that of the adsorbed enzyme recovered only 70–75% of its third day level with washing. If one extrapolates back to zero time, it may be noted that the coupled enzyme is loaded only to approximately 80% of that of the adsorbed enzyme. However, after about 10 days of operation, these columns are about equal in activity. The half-life of the adsorbed column, column #1, is approximately 16 days, while that of the coupled enzyme, column #2, is about 26 days.

The half-lives discussed are apparent half-lives, since these columns can be restored to higher levels of activity with water washing. In an attempt to gain information with respect to the true half-life, one would have to again extrapolate back to zero time for each column and determine the losses of activity at a point when the columns were thoroughly washed. By utilizing this procedure, the calculated half-life for the adsorbed column is approximately 41 days, while that of the coupled column is 107 days.

EXAMPLE III

Anti-digoxin Antibodies Coupled to Titania Particles

It is well known that immobilized antibodies (IMA) can be used in a variety of applications requiring a high degree of chemical specificity (e.g. antigen or hapten purification from a mixture of molecules and solid-phase radioimmunoassays (SPRIA) to detect and determine concentrations of various substances). In this example, goat anti-digoxin antibodies which had been dialyzed against 0.01 M phosphate buffer at pH 7.4 were coupled via the PAPI 901 to titania particles having an average particle size of 320A and a surface area of 48 $m^2/g$. The anti-digoxin antiserum contained 66.5 mg protein per ml by the Folin Phenol method and 42.75 mg protein N/ml by the hydrolysis-Ninhydrin determination. The antiserum bound 50% of 0.8 mg of $^3H$ digoxin at a dilution of 1:45,000. The polymeric isocyanate solution consisted of 0.1 ml of the PAPI-901 diluted to 20 ml with acetone (50 mg of the isocyanate per 10 ml). The titania carrier in this example was non-porous to eliminate or minimize diffusion effects in the subsequent assays.

Coupling Procedure 1 gm quantities of the titania were transferred to each of two Erlenmeyer flasks (25 ml) to prepare 2 samples, IMA #1 and IMA #2. To each flask 10 ml of coupling solution (50 mg PAPI 901) was added. The contents were mixed and the flasks were stoppered and permitted to stand at room temperature for 1 hour and 10 minutes. During this time the coupling solution, which had been yellow due to the presence of the coupling agent, turned colorless. The colorless acetone solvent was decanted and 1.25 ml of the anti-digoxin was added to each flask containing the isocyanated titania followed by the addition of 5 ml of 0.01 molar phosphate buffer, pH 7.4, to each flask. The flasks were placed in a reciprocal shaker and shaken at room temperature for 1 hour and 10 minutes. The samples were then transferred to respective 30 ml centrifuge tubes with the aid of water addition to about a 25 ml total level. The contents of the centrifuge tubes were mixed with a vortex mixer followed by stirring with a Teflon TM stirring rod. The tubes with contents were centrifuged in a clinical centrifuge at top speed for 2 minutes. The clear supernatant fluid was decanted and saved from each tube for protein analysis. The sediments in the centrifuge tubes were then washed with 15 ml of buffer, mixed, and recentrifuged as above. This wash with buffer was repeated two more times and all of the washes were pooled from each sample for protein analysis.

Control

An identical experiment was performed as above utilizing an anti-rabbit gamma globulin from the goat which contained no anti-digoxin activity as a control. The antiserum showed no reaction in a soluble system with digoxin. It contained 49.90 mg protein N/ml by the Ninhydrin method and 77.0 mg/ml by the Folin Phenol determination.

Blank

The blank carrier was prepared with the same quantity of coupling agent utilizing the same procedure except that no protein was added to the carrier.

Dry Weight Determination

The covalently coupled immobilized antiserum wet cakes (IMA #1 and IMA #2) were analyzed first for their dry weight and protein nitrogen content. Portions of the wet cake were dried in hot air ovens (110° C) overnight and the weight difference calculated to obtain dry weight.

Protein Nitrogen Determination by Ninhydrin Method

A portion of the wet cake was prepared as a 1% suspension in phosphate buffered saline (PBS). Ninhydrin protein nitrogen determinations were performed on 1 ml portions of these IMA suspensions. All washes following the coupling reaction were also assayed for protein nitrogen.

Biological Activity Determination

The same 1% IMA suspension was assayed also for its biological activity. Dilutions of the IMA's were prepared in stabilized phosphate buffered saline (SPBS) so that duplicate ml aliquots were reacted with 0.050 ml of $^3H$-Digoxin (0.8 ng digoxin). The PBS consisted of 0.01 M phosphate in 0.15 M NaCl. The stabilized PBS (SPBS) was prepared by the addition of 1 mg of bovine serum albumin (BSA) and 0.02% $NaN_3$.

The reaction was performed at room temperature for 10 min. The reaction tubes, with total count and blank controls, were centrifuged at 4500 rpm and 5° C for 30 min. The supernatant solutions containing the free (unbound) $^3H$-Digoxin were decanted into liquid scintillation vials containing 10 ml of Aquasol (New England Nuclear) and counted for 1 min. in a Packard TriCarb Liquid Scintillation Spectrometer, Model 3320. The percent $^3H$-Digoxin bound was determined by calculating the ratios between total free counts in the tests and the counts after reaction with IMA. The results were made into a graph and the 50% binding points determined.

Solid-Phase Radioimmunoassay

The IMA's were used to perform a SPRIA. The dilutions from a 1% suspension of IMA calculated to bind 50% of $^3H$-Digoxin were added to 0.2 ml volumes of human plasma containing digoxin concentrations of 0.5 to 10 ng/ml. The total volume was 1 ml to which was added 0.05 ml of $^3H$-Digoxin. The reagents were mixed and reacted for 10 min. at room temperature, and the bound and unbound $^3H$-Digoxin separated and calculated as described above. The results were analyzed statistically by a computerized two variable linear regression.

Results

Dry Weight and Protein Analysis

The IMA complexes were relatively uniform with respect to protein N/g dry weight of support. The procedure coupled an average of 97.5% of the protein N offered, and an average of 102.88% of protein N was recovered. The 26.2 mg of protein N/g dry weight of carrier (4.2 mg N/g) on the $TiO_2$-polyisocyanate control can be attributed to the presence of ligand itself (i.e., PAPI, polymethylene polyphenyl isocyanate). The ninhydrin nitrogen determination was performed with aqueous reagents which produce a primary amine in place of the residual isocyanate group.

Biological Activity

Only those IMA complexes prepared with digoxin specific goat anti-digoxin serum demonstrated activity. The control $TiO_2$ support-ligand and goat anti-rabbit gamma globulin IMA complexes were completely negative.

Solid-Phase Radioimmunoassay

Representative curves of IMAs #1 and #2 were prepared. Analyses of these curves indicate correlations of 97.4%. These curves could be used to detect and quantitate 0.5 to 10.0 ng of digoxin/ml of human plasma. The results and properties of the two samples (IMA #1 and IMA #2) are compared with the control (anti-rabbit gamma globulin) and blank (no antibody) in Table III.

TABLE III

Biological Activity and Solid-Phase Radioimmunoassay of $TiO_2$-PAPI-Antiserum Complexes, a control, and a blank.

| IMA COMPLEX NO. | 1 | 2 | 3 | Blank |
|---|---|---|---|---|
| Antiserum (Goat) | Anti-digoxin | Anti-digoxin | Anti-rabbit Gamma Globulin | No Ab |
| 1% Suspension: | | | | |
| mg Dry wt/ml | 1.90 | 1.82 | 1.66 | 2.34 |
| μg Protein N/ml | 99.80 | 101.50 | 98.30 | 61.30 |
| 50% Binding of $^3$H-Digoxin: | | | | |
| Dilution from 1% suspension | 1:15 | 1:10 | No Binding | No Binding |
| μg IMA | 126.50 | 182.00 | — | — |
| μg Protein N | 6.65 | 10.15 | — | — |
| Titer of Antiserum: | | | | |
| To Bind 50% of $^3$H-Digoxin | 1:45,000 | 1:45,000 | — | — |
| μg Protein N for 50% Binding | 0.95 | 0.95 | — | — |
| Activity Recovered, % | 14.30 | 9.35 | — | — |
| SPRIA: | | | | |
| Δ% Binding (0–10 ng/ml) | 29.0 | 31.5 | — | — |
| Slope | 0.580 | 0.563 | — | — |

From the above, it was found that the procedures for covalently coupling antiserum to $TiO_2$-polymeric isocyanate ($TiO_2$-PAPI) derivative demonstrated several advantages: (1) The $TiO_2$-PAPI derivative is fast and easy to prepare. (2) The speed of the antiserum coupling step rivals those of previously used Schiff-base and thiourea reactions using Silanized inorganics. (3) The efficiency of antiserum protein N coupling averaged 97.5% (93.3–104.2%) which compared favorably to an average of 81.7% (73.48–91.25%) for azo-linkage to arylamine-(organic solvent silanization) bonding techniques, 70.5% (67.5–73.5%) for Schiff-base using glutaraldehyde and alkylamine-porous glass carriers, and 107.1% (87.5–121.5%) for the thiourea bonding method.

The percent of activity recovered was a low average of 11.675%, compared to a range of 17% to 49.5% by azo-linkage to arylamine CPG. The difference may result from the isocyanate derivatization step which had not been optimized and which may have been cross-linking the anti-serum protein excessively. The overall procedure has the following advantages: (1) low cost and ready availability of materials and reagents; (2) rapidity of producing the polyisocyanate derivative; (3) the ease of coupling antiserum to the derivative; and (4) the high rate of coupling efficiency.

Other Ways of Utilizing Polymeric Isocyanate Coupling Agent

It may be desirable to couple an enzyme through other than an isocyanate group. It this were the case, then an organic amine or hydroxyl compound with another functional group could be directly attached to the isocyanate. Another approach could be to react the isocyanate after it is coupled to the carrier with water. Water reacts with the isocyanate to produce carbon dioxide and results in the production of an amine on the original coupling agent in place of the isocyanate group. This amine could be treated in the same fashion as the amine on silane coupling agents for either modification or attachment to other functional molecules such as glutaraldehyde, etc.

Inasmuch as the above-described procedures for bonding biologically active proteins to inorganics are subject to modification, it is intended that the examples should be construed as illustrative and that the invention should be limited only by the appended claims.

We claim:

1. A method of immobilizing biologically active proteins on the surfaces of a water insoluble porous high surface area inorganic material, the method comprising the steps of reacting a high surface area inorganic material having surface hydroxyl or oxide groups with an organic solution of a polymeric isocyanate represented by the formula

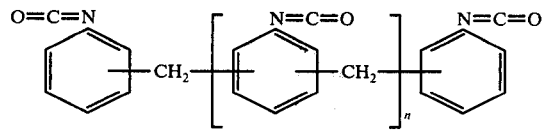

where n is at least 2, said reaction resulting in inocyanate groups of the polymeric isocyanate reacting with said hyroxyl or oxide groups of said material to form a carbonate and the reaction being under conditions sufficient to form a surface of free isocyanate groups on the material, and then reacting the material with a dispersion of biologically active proteins under conditions sufficient to bond the proteins to the material in a biologically active state.

2. The method of claim 1 wherein the inorganic material consists of high surface area titania, silica, alumina, or porous glass.

3. The method of claim 1 wherein the protein is an enzyme.

4. The method of claim 3 wherein the enzyme is selected from papain, urease, glucoamylase, and lactase.

5. The method of claim 1 wherein the protein is an antibody.

6. The method of claim 5 wherein the antibody is an antibody to digoxin.

7. The method of claim 1 wherein the polymeric isocyanate solution comprises a solution of polymeric isocyanate in acetone.

8. An immobilized biologically active composite comprising proteins bonded to a high surface area inorganic support material, the composite produced in accordance with the method of claim 1.

* * * * *

UNITED STATES PATENT AND TRADEMARK OFFICE
CERTIFICATE OF CORRECTION

PATENT NO. : 4,071,409
DATED : January 31, 1978
INVENTOR(S) : Ralph A. Messing and Sidney Yaverbaum It is certified that error appears in the above-identified patent and that said Letters Patent are hereby corrected as shown below:

Column 10, Claim 1, line 37, "carbonate" should be -- carbamate --.

Signed and Sealed this

Second Day of January 1979

[SEAL]

Attest:

RUTH C. MASON
Attesting Officer

DONALD W. BANNER
Commissioner of Patents and Trademarks